United States Patent [19]

Vidic et al.

[11] Patent Number: 5,206,265
[45] Date of Patent: Apr. 27, 1993

[54] IRON CITRATE COMPLEX, PROCESS FOR ITS PRODUCTION, AND ITS PHARMACEUTICAL

[75] Inventors: Hans-Jörg Vidic, Berlin, Fed. Rep. of Germany; Eraldo Antonini, deceased, late of Rome, Italy, by Virginia Antonini, Giovanni Antonini, Paola Antonini De Somma, Andrea Antonini, Cristina Antonini, executors

[73] Assignee: Schering Aktiengesellschaft, Berlin and Bergkamen, Fed. Rep. of Germany

[21] Appl. No.: 646,789

[22] PCT Filed: Sep. 9, 1988

[86] PCT No.: PCT/DE88/00568
§ 371 Date: Mar. 23, 1992
§ 102(e) Date: Mar. 23, 1992

[87] PCT Pub. No.: WO89/02426
PCT Pub. Date: Mar. 23, 1989

[30] Foreign Application Priority Data

Sep. 14, 1987 [IT] Italy ................................ 21904 A/87

[51] Int. Cl.⁵ ..................... A61K 31/295; C07F 15/02

[52] U.S. Cl. .................................. 514/502; 514/814; 556/147

[58] Field of Search ................. 556/147; 514/502, 814

[56] References Cited

U.S. PATENT DOCUMENTS

| 2,904,573 | 9/1959 | Orosnik et al. | 260/439 |
| 2,955,981 | 10/1960 | Linkenheimer | 167/53 |
| 2,957,806 | 10/1960 | Rummel | 167/68 |
| 3,873,588 | 3/1975 | Osawa et al. | 260/439 R |
| 4,400,535 | 8/1983 | Madaus et al. | 562/584 |

FOREIGN PATENT DOCUMENTS

| 0682724 | 11/1952 | United Kingdom | 556/147 |
| 0906418 | 9/1962 | United Kingdom | 556/147 |

Primary Examiner—José G. Dees
Assistant Examiner—Porfirio Nazario
Attorney, Agent, or Firm—Millen, White, Zelano & Branigan

[57] ABSTRACT

The invention relates to an iron citrate micellar complex having a composition of 10.6% carbon, 2.62% hydrogen, 50.2% oxygen, 32% iron, and 4.6% sodium; a molecular weight of about 33,000 (HPLC-LALLS measurement); and the empirical formula $(C_{31}H_{92}O_{110}Fe_{20}Na_7)_n$; to a process for its production; and to its pharmaceutical use.

5 Claims, No Drawings

IRON CITRATE COMPLEX, PROCESS FOR ITS PRODUCTION, AND ITS PHARMACEUTICAL

The present invention relates to a novel iron citrate complex, process for its production, and its pharmaceutical use.

Iron compounds with di- and trivalent iron, as well as iron chelates of a low or relatively high molecular weight have been utilized for a long time for the therapy of iron deficiency anemia. Most of these iron preparations, when used on a long-term scale, lead to gastrointestinal complications or exhibit a certain toxicity. In contrast thereto, ferritin proved to be an agent of local as well as general compatibility. However, ferritin has the drawback that it is available only in limited amounts because, besides horse spleen, there are no raw material sources for ferritin worth mentioning.

Therefore, it is an object of the invention to provide an iron compound, the micellar structure of which is very similar to the structure of the micelles of the ferritin nucleus, without concomitantly losing the favorable pharmaceutical and toxicological properties of ferritin.

Japanese Laid-Open Application JP 18 798/61 discloses a process for the production of a water-soluble iron complex from alkali citrate and iron carbonate. The iron carbonate, formed from 1 mole of $FeCl_3.6H_2O$ and 1.5 moles of sodium bicarbonate at temperatures of below 13° C. is reacted with sodium citrate to form an iron complex salt consisting of about 60% iron.

It has now been discovered surprisingly that a brown-colored iron citrate micellar complex is produced from $FeCl_3.6H_2O$, $NaHCO_3$ and trisodium citrate exhibiting the following properties:

(a) composition: 10.6% carbon, 2.62% hydrogen, 50.2% oxygen, 32% iron, 4.6% sodium;
(b) molecular weight about 33,000 (HPLC-LALLS measurement);
(c) empirical formula $(C_{31}H_{92}O_{110}Fe_{20}Na_7)_n$ wherein $n=9-10$;
(d) soluble in water, glycerol-water mixtures, practically insoluble in conventional organic solvents;
(e) ultraviolet absorption in water: $\lambda max$ (470 nm) $E_1$ $cm^{1\%} = 23-26.5$;
(f) resistance (1% strength solution) 600–750 $\Omega.cm$;
(g) turbidity pH (1% strength solution) 2.6–2.8.

This novel iron citrate complex is stable even in low pH ranges, thus having the advantage of passing through the stomach as an active agent without decomposition. The composition of the novel complex varies within the range customary for elementary analyses. Consequently, the indicated composition merely represents an average value, and the novel complex is not to be restricted to this value.

The iron citrate complex according to the invention is distinguished by extraordinary stability. Thus, solutions of the novel complex in a water/glycerol mixture (40:60) stored at room temperature proved to be stable even after 3 years. They showed no signs of decomposition whatever, i.e. there was no separation of flocculent precipitate, for example.

The novel complex is found to be an extensively unitary polymeric compound in all investigations. Thus, the electropherogram of a solution of this complex in a buffer on cellulose acetate film showed in all cases only one uniform band.

Further analyses yielded a content of bound citrate of about 28% for the complex.

The invention likewise relates to a process for the production of the iron citrate micellar complex having the above-disclosed properties, characterized by adding solid $NaHCO_3$ to an aqueous solution of $FeCl_3.6H_2O$, removing the thus-released $CO_2$ from the solution with an inert gas or by vacuum degasification, adding solid trisodium citrate, and precipitating from the thus-obtained solution, after a relatively long period of equilibrating at room temperature, the product of the process with methanol.

Instead of using methanol precipitation, the product of the process can also be obtained by dialysis or gel filtration and subsequent freeze-drying. However, methanol precipitation is preferred.

The invention furthermore concerns medicinal agents containing the iron citrate micellar complex of this invention and nontoxic, pharmaceutically harmless extenders and auxiliary agents. Among these extenders and auxiliary agents are all substances and compounds known to a person skilled in this field of art. The novel complex can also be administered in combination with folic acid. The novel agent is likewise suited for the treatment of diseases involving iron deficits. The iron citrate complex utilized for the treatment of iron deficiencies in children, women, reconvalescent persons, high-performance athletes can be administered in the form of solutions, capsules, dragees, and tablets.

The novel iron citrate complex exhibits improved pharmacological and toxicological properties as compared with ferritin.

When administering various iron preparations to male Wistar rats (weight 150–170 g), the iron blood values rise more vigorously upon administration using the novel complex than with ferritin or with $FeSO_4$ (measured as serum iron in $\mu g$ % after 6 hours of treatment).

The novel complex is nontoxic even at high doses of >800 mg/kg. In tests on rats, no change of the gastric mucosa whatever was observed even after 1, 3 and 7 days.

EXAMPLE 1

Under agitation, 2.5 equivalents of $NaHCO_3$ is added to a 0.3-molar aqueous $FeCl_3$ solution (prepared from $FeCl_3. 6H_2O$ by dissolving in water). Then $CO_2$ is removed from the dark brown colored solution either by introducing an inert gas (nitrogen or argon) or by vacuum degasification. As soon as the largest portion of $CO_2$ has been removed, an amount of solid trisodium citrate stoichiometric with respect to the iron is added under shaking, and the solution is thereupon allowed to stand at room temperature for up to 20 hours. The resultant solution is clear, shows an intense color, and has an almost neutral pH.

Thereafter, the solution is dialyzed against water or phosphate buffer (pH 7, 0.1–0.01-molar) in order to remove all ingredients having a low molecular weight. A measure for the progress of the dialysis is the conductivity of the dyalizate which, when using the unconcentrated solution, is to have a value of about 700 $\Omega.cm$. This process step of demineralizing can also be performed by means of gel filtration over a column, with "Sephadex" G 25 (Pharmacia) in 2.5% citrate buffer. The solution is freeze-dried up to a moisture content of about 2%. The yield of iron micelles, based on Fe(III) chloride employed, is 31%.

The yield, based on iron (=corrected theoretical yield): 66%.

Elementary analysis: C 10.65%; H 2.66%; Na 4.5%; Fe 32.76%.

Extinction (0.1% solution at 470 nm): 1.06.

pH (1% strength solution): 7.8.

Specific extinction (based on 1% iron content): 23.9.

pH at which turbidity occurs (1% strength solution): 2.9.

Water content (according to K. Fischer in %): 2.1.

EXAMPLE 2

A solution of 8.1 g (0.03 mol) of $FeCl_3.6H_2O$ in 95 ml of deionized water is provided. Within 10 minutes, 6.3 g (0.075 mol) of sodium bicarbonate is added in solid form under agitation. During this step, there is a strong release of gas ($CO_2$), and the pH rises to 2.5.

For removal of carbon dioxide, nitrogen is sparged through the solution for about 1 hour. Then 8.8 g (0.03 mol) of trisodium citrate.$2H_2O$ is added all at once under agitation. The thus-formed precipitate is dissolved again after about 5 minutes, the pH rising to 5.7. After an agitation period of 30 minutes, a pH of 6.4 can be measured. The solution is allowed to stand without stirring for about 15 hours. During this time, the pH increases to about 7.9.

The resultant solution (110 ml) is combined under agitation with 88 ml of methanol. The precipitated product is further st for 30 minutes and then suctioned off by way of a suction filter. The filter cake is suspended in 55 ml of water/methanol mixture (1+2) by means of a turbine mixer, again suctioned off, and washed with 15 ml of methanol. The residue is dried thereafter at 50° C.

The yield is 3.60 g (85% of the iron utilized).

Elementary analysis: C 10.56%; H 2.60%; Na 4.8%; Fe 30.98%.

Extinction (0.1% solution at 470 nm): 0.912.

pH (1% strength solution): 7.9.

Resistance (1% strength solution): 607.5 $\Omega.cm$.

Specific extinction (based on 1% iron content): 25.55.

pH at which turbidity occurs (1% strength solution): 2.66.

Water content (according to K. Fischer in %): 6.15.

We claim:

1. An iron citrate micellar complex, which is a brown solid having the properties set out below:
   (a) average composition by weight of about: 10.6% carbon, 2.62% hydrogen, 50.2% oxygen, 32% iron, 4.6% sodium;
   (b) molecular weight about 33,000 (HPLC-LALLS measurement);
   (c) empirical formula $(C_{31}H_{92}O_{110}Fe_{20}Na_7)_n$ wherein n=9–10;
   (d) soluble in water, glycerol-water mixtures, practically insoluble in conventional organic solvents;
   (e) ultraviolet absorption in water; $\lambda max$ (470 nm); $E_{1\ cm}^{1\%}$=23–26.5;
   (f) resistance (1% strength solution) 600–750 $\Omega.cm$;
   (g) turbidity pH (1% strength solution) 2.6–2.8.

2. A process for producing the iron citrate micellar complex of claim 1, wherein solid $NaHCO_3$ is added to an aqueous solution of $FeCl_3.6H_2O$, the thus-released $CO_2$ is removed from the solution with an inert gas or by vacuum degasification, solid trisodium citrate is added, and, after a relatively long period of allowing the solution to stand at room temperature, the product of the process is precipitated from the thus-obtained solution with methanol.

3. The process of claim 2, wherein, instead of methanol precipitation, a dialysis or a gel filtration and freeze-drying is performed.

4. A medicinal agent, containing the iron citrate micellar complex as claim 1 and nontoxic, pharmaceutically harmless extenders and auxiliary agents.

5. The medicinal agent of claim 4 which further contains folic acid.

* * * * *